United States Patent
Gould et al.

(10) Patent No.: US 8,808,756 B2
(45) Date of Patent: Aug. 19, 2014

(54) COPPER CONTAINING ALGICIDAL COMPOUNDS

(75) Inventors: Rachael A. T. Gould, Forest Lake, MN (US); Rebecca L. Everman, St. Paul, MN (US); Jamieson C. Keister, Lakeville, MN (US); Kathleen K. Reynolds, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 112 days.

(21) Appl. No.: 12/444,800

(22) PCT Filed: Oct. 11, 2007

(86) PCT No.: PCT/US2007/081061
§ 371 (c)(1),
(2), (4) Date: Apr. 8, 2009

(87) PCT Pub. No.: WO2008/045992
PCT Pub. Date: Apr. 17, 2008

(65) Prior Publication Data
US 2010/0098777 A1    Apr. 22, 2010

Related U.S. Application Data

(60) Provisional application No. 60/829,462, filed on Oct. 13, 2006.

(51) Int. Cl.
*A01N 59/20* (2006.01)
*B32B 5/16* (2006.01)
*B32B 3/26* (2006.01)
*A01P 13/00* (2006.01)

(52) U.S. Cl.
USPC ...... 424/630; 428/328; 428/319.1; 427/372.2

(58) Field of Classification Search
None
See application file for complete search history.

(56) References Cited

U.S. PATENT DOCUMENTS

| 4,450,282 | A  | * | 5/1984  | Ritzer et al. ............. 556/472 |
| 5,382,475 | A  |   | 1/1995  | Kayser |
| 6,214,466 | B1 |   | 4/2001  | Joedicke |
| 6,569,520 | B1 |   | 5/2003  | Jacobs |
| 6,585,813 | B2 |   | 7/2003  | Kiik |
| 2004/0139886 | A1 |   | 7/2004  | Joedicke |
| 2004/0255548 | A1 |   | 12/2004 | Hong |
| 2005/0142329 | A1 | * | 6/2005  | Anderson et al. ......... 428/143 |
| 2007/0116987 | A1 | * | 5/2007  | Khan et al. .............. 428/701 |
| 2007/0740702 |    |   | 9/2007  | Jacobs |

FOREIGN PATENT DOCUMENTS

| CA | 2 122 080 | 4/2007 |
| CA | 2 375 459 | 8/2010 |

OTHER PUBLICATIONS

Detection of active oxidative species in TiO2 photocatalysts using the fluorescence technique Ishibashi, K; et al. Electrochem. Comm. 2 (2000) 207-210.
"Quantum yields of active oxidative species formed on TiO2 photocatalyst" Ishibashi, K; et al. J. Photochem. and Photobiol. A: Chemistry 134 (2000) 139-142.

* cited by examiner

*Primary Examiner* — Sue Liu
*Assistant Examiner* — Erin Hirt
(74) *Attorney, Agent, or Firm* — Craig A. Deutsch

(57) ABSTRACT

The present application is directed to a coating composition comprising a ceramic binder and inorganic copper compound particles. Generally, the inorganic copper compound particles have a median particle size of less than 5 micrometers. In some embodiments, the particles have a median particle size of greater than 1 micrometer. The inorganic copper compound particles may be non-photocatalytic. The coating may also be placed on a structural layer.

47 Claims, 1 Drawing Sheet

COPPER CONTAINING ALGICIDAL COMPOUNDS

BACKGROUND

The present invention relates to algaecidal compounds containing copper. Copper is a known algaecide and fungicide.

Inorganic substrates have been coated with compositions that contain pigments to impart color properties to the substrate for aesthetic purposes. The coated substrates are generally applied or affixed to specific carriers to provide a desired color to the object. For example, coated inorganic granules are often utilized on granule-surfaced bituminous roll roofing and asphalt shingles. The granules, which are partially embedded in one surface of asphalt-impregnated shingles or asphalt-coated fiber sheet material, form a coating which provides an inherently weather-resistant, fire resistant, and decorative exterior surface. The layer of roofing granules functions as a protective layer to shield the bituminous material and the base material from both solar (e.g. ultraviolet radiation) and environmental degradation.

Inorganic substrates are generally coated by applying a slurry containing an inorganic binder and pigment particles onto the substrate. In granular form, the inorganic material is heated in a rotary kiln and mixed with the slurry of inorganic binder and pigment particles. The coated inorganic granules are first dried and then fired at temperatures in excess of 170° C. to insolubilize the binder. The resulting coated granule has a hardened coating that exhibits a selected coloring due to the inclusion of the pigments.

Coated granules are often produced and selected to provide a desirable color to a finished structure or building. It is desirable that the color be consistent over time in order to maintain the appearance of the building. Discoloration of roofing shingles and other building materials due to algae infestation has become especially problematic in recent years. Algae tend to grow on building materials in areas where moisture is retained. Discoloration has been attributed to blue-green algae, *Gloeocapsa* spp., transported as air-borne particles. The infestation may be particularly acute on asphalt shingles.

Copper compound particles are added to coatings to form algae resistant coatings. The copper ions in the compounds are released, or leached, over time as the coating is subjected to weathering and water. It is known to use copper compound particles in coatings that have a median particle size of about 7 micrometers or greater.

SUMMARY

Currently, coatings use a high amount of copper compound (for example if the inorganic copper compound is cuprous oxide, the weight percent is in excess of 50 weight percent solids of the coating and in excess of 5 or 6 weight percent of resulting coated roofing granules) loaded into the coatings, resulting in a waste of useful copper because the center of the inorganic copper particles do not leach at a useful rate. It is desired to improve the efficiency of the release of copper ions, so that the amount of copper used in the algae resistant coatings can be reduced, while maintaining the life expectancy of the algae resistant coatings. It would be an advantage to provide a coating composition comprising a ceramic binder and inorganic copper compound particles. Generally, the inorganic copper compound particles have a median particle size of less than 5 micrometers. In some embodiments, the particles have a median particle size of greater than 1 micrometer. The inorganic copper compound particles may be non-photocatalytic. The coating may also be placed on a structural layer.

DETAILED DESCRIPTION

Ceramic Binder

Figure 1:
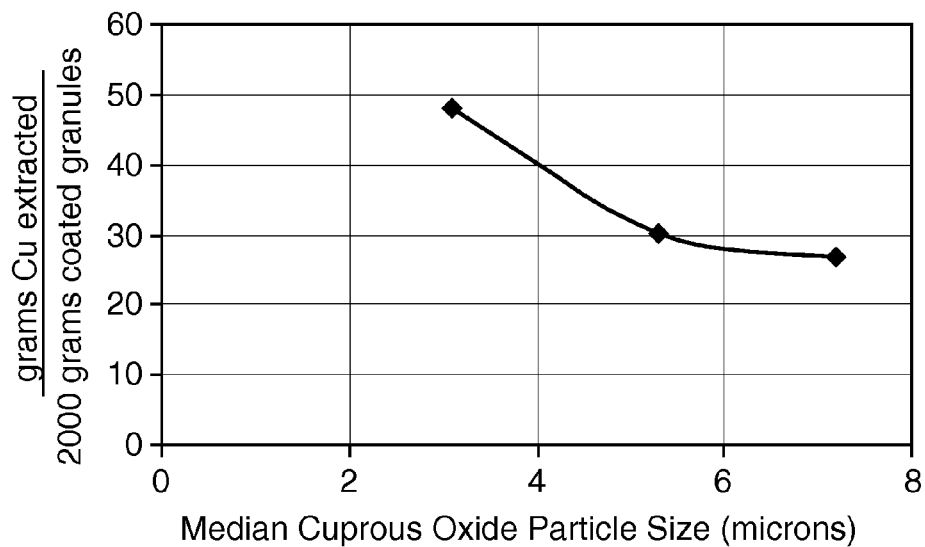
FIG. 1 shows the Main Effects Plot of the average total copper extracted from the coating after 10 extractions for different median particle size cuprous oxide.
Figure 2:
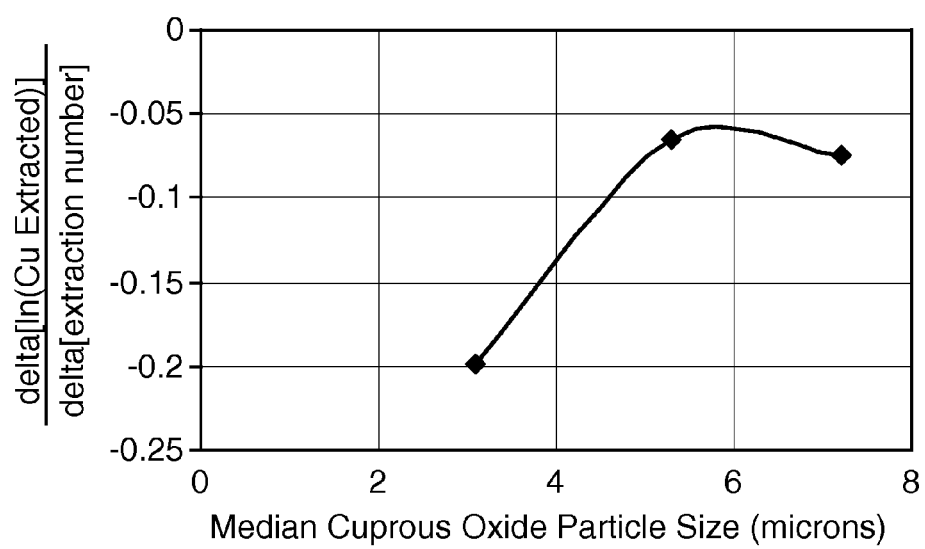
FIG. 2 shows the Main Effect Plot the logarithmic rate of the copper extracted per extraction step for cuprous oxide of various median particle size.

The coating composition of the present invention is generally an aqueous slurry containing an inorganic binder and a plurality of inorganic cuprous compound particles. The function of the inorganic binder in the composition is to adhere the coating to a desired inorganic substrate. Preferably, the inorganic binder is an alkali metal silicate binding agent. Alkali silicate binding agents include those selected from the group consisting of lithium silicate, potassium silicate, sodium silicate, or combinations thereof. The alkali metal silicate is generally designated as $M_2O:SiO_2$, where M is lithium, potassium, or sodium. The weight ratio of $SiO_2$ to $M_2O$ ranges from about 1.4:1 to about 3.75:1. Preferably, the weight ratio is in the range of about 2.75:1 to about 3.22:1. At about 38% to about 41% solids in solution, the amount of inorganic binder included in the coating composition is in the range of about 14 to about 30 parts by weight per thousand parts by weight of granules, and preferably in the range of about 17 to about 22 parts by weight per thousand parts by weight of granules.

In accordance with the inventive composition, an aluminosilicate compound may optionally be added to the composition in order to neutralize the binder. Conventional aluminosilicate compounds are suitable for use with the present invention. Examples of suitable aluminosilicate clays include kaolin clay having the formula $Al_2Si_2O_5(OH)_4$. The aluminosilicate compound is included in the composition in an amount sufficient to achieve a ratio of, for example, up to 15 parts by weight of aluminosilicate per 1000 parts by weight granules. In other embodiments, the ratio is up to 20 parts by weight and in some embodiments is up to 25 parts by weight. Preferably, the ratio is 7 to 13 parts by weight of aluminosilicate per 1000 parts by weight granules. The particle size of the aluminosilicate compound may vary. However, it is generally preferred that the aluminosilicate contain less than 0.5 percent coarse particles (particles greater than 0.002 millimeters in diameter).

Inorganic Copper Compound

The coating of the present invention contains inorganic copper compound particles. In certain embodiments, the copper compound may be cuprous, for example cuprous oxide. In other embodiments, the copper compound is cupric, for example cupric oxide. Other useful inorganic copper compounds include cupric bromide, cupric stearate, cupric sulfate, cupric sulfide, cuprous cyanide, cuprous thiocyanate, cuprous stannate, cupric tungstate, cuprous mercuric iodide, and cuprous silicate, or mixtures thereof. The inorganic copper compound may be photocatalytic or non-photocatalytic.

Generally, the particles have a median particle size of less than 5 micrometers. In certain embodiments, the particles have a median particle size of less than 4 micrometers, for example less than 3 micrometers.

Generally, the copper compound particles have a median particle size greater than zero (0). In certain embodiments, the particles have a median particle size of greater than 5 nanometers, for example greater than 10 nanometers and greater than 20 nanometers. In some embodiments, the copper compound is greater than 1 micrometer, for example 1.2 micrometer.

In specific embodiments, the copper compound particles have a median particle size of greater than 2.5 micrometers, for example greater than 2.8 micrometers. In specific embodiments, the median particle size is 2.9 to 3.0 micrometers.

The median particle size is determined by the Electrical Sensing Zone Method (sometimes seen described as the "Coulter Technique"), such as used in a Coulter Multisizer™ 3 particle size analyzer, available from Beckman Coulter Inc., Fullerton Calif.

Additionally, the copper compound has a surface area. Surface area can be measured using the BET (Brunauer, Emmit, and Teller) technique for measuring surface area using a Quantchrome Autosorb-1 instrument to measure nitrogen gas physical adsorption onto the samples. Surface area is dependent on the particle size, particle shape and the porosity of the copper compound. Generally, the surface area for the copper compound particle is greater than 0.3 $m^2$/gram. In some embodiments, the surface area is greater than 0.5 $m^2$/gram, for example, greater than 1 $m^2$/gram and in specific embodiments, greater than 2 $m^2$/gram.

Generally, if the inorganic copper particle is cuprous oxide, the particles are loaded into the ceramic binder at from 1 to about 60 weight percent solids of the coating.

Additives

Photocatalysts, upon activation or exposure to sunlight, establish both oxidation and reduction sites. Photocatalytic particles include those particles treated, shielded or coated to inhibit the photocatalytic activity of the particle. These sites are capable of preventing or inhibiting the growth of algae on the substrate or generating reactive species that inhibit the growth of algae on the substrate. In other embodiments, the sites generate reactive species that inhibit the growth of biota on the substrate. The sites themselves, or the reactive species generated by the sites, may also photooxidize other surface contaminants such as dirt or soot or pollen. Photocatalytic elements are also capable of generating reactive species which react with organic contaminants converting them to materials which volatilize or rinse away readily.

Photocatalytic particles conventionally recognized by those skilled in the art are suitable for use with the present invention. Suitable photocatalysts include, but are not limited to, $TiO_2$, $ZnO$, $WO_3$, $SnO_2$, $CaTiO_3$, $Fe_2O_3$, $MoO_3$, $Nb_2O_5$, $Ti_xZr_{(1-x)}O_2$, $SiC$, $SrTiO_3$, $CdS$, $GaP$, $InP$, $GaAs$, $BaTiO_3$, $KNbO_3$, $Ta_2O_5$, $Bi_2O_3$, $NiO$, $Cu_2O$, $SiO_2$, $MoS_2$, $InPb$, $RuO_2$, $CeO_2$, $Ti(OH)_4$, combinations thereof, or inactive particles coated with a photocatalytic coating.

In other embodiments, the photocatalytic particles are doped with, for example, carbon, nitrogen, sulfur, fluorine, and the like. In other embodiments, the dopant may be a metallic element such as Pt, Ag, or Cu. In some embodiments, the doping material modified the bandgap of the photocatalytic particle. In some embodiments, the transition metal oxide photocatalyst is nanocrystalline $TiO_2$ and in some embodiments, the transition metal oxide photocatalyst is nanocrystalline ZnO.

Relative photocatalytic activities of a substrate, substrate coating and/or coated substrate can be determined via a rapid chemical test that provides an indication of the rate at which hydroxyl radicals are produced by UV-illuminated photocatalyst in or on the substrate. One method to quantify the production of hydroxy radicals produced by a photocatalyst is through use of the 'terephthalate dosimeter' which has been cited numerous times in the open literature. Recent publications include: "Detection of active oxidative species in TiO2 photocatalysts using the fluorescence technique" Ishibashi, K; et. al. Electrochem. Comm. 2 (2000) 207-210. "Quantum yields of active oxidative species formed on TiO2 photocatalyst" Ishibashi, K; et al. J. Photochem. and Photobiol. A: Chemistry 134 (2000) 139-142. In particular cases, useful photocatalytic materials include $TiO_2$, $WO_3$, ZnO and similar wide-bandgap semiconducting metal oxides. In some instances, photocatalysts include the anatase form of $TiO_2$ and or mixtures of anatase $TiO_2$ and rutile $TiO_2$. In some instances, photocatalysts include mixtures of $TiO_2$ and ZnO.

Photocatalysts are further described in U.S. Pat. No. 6,569,520, and US Patent Application US2005/0142329 (Ser. No. 10/746,829), assigned to 3M Innovative Properties Company.

Additional additives in the presently described coating include pigments. Pigments may be included in the composition to achieve a desired color property. Suitable pigments would include, for example, compounds such as carbon black, titanium dioxide, chromium oxide, yellow iron oxide, phthalocyanine green and blue, ultramarine blue, red iron oxide, metal ferrites, and mixtures thereof. Other conventional pigments are also suitable for use with the present invention. Those skilled in the art are capable of determining amounts of additional pigments needed in a composition to achieve a specific color property. The mean particle sizes of the noted pigments may vary.

Dispersants may be added to the composition to assist in dispersing the optional pigment particles, throughout the composition. The appropriate level of dispersion of particles in the slurry will assist in achieving a coating on a granular substrate having a greater uniformity in color. Both anionic and non-ionic dispersants may be suitable for use with the present invention. The dispersant is typically used in an amount ranging up to about 20 weight percent of the pigment particles, and preferably up to about 10 weight percent of the pigment particles. An example of a dispersant is the sodium salt of sulfonated naphthalene-formaldehyde condensate marketed as Rhodacal N from Rhodia in Cranbury, N.J.

Additives may also include reflective particles, for example additives that reflect infrared light. Examples include those described in U.S. Patent Application US2007/740702 (Ser. No. 11/601,094), assigned to 3M Innovative Properties Company.

Structural Layer

The structural layer may be any layer, especially those used in construction. For example, the structural layer may be an interior or exterior construction surface. A construction surface is a surface of something man-made. The structural layer may be horizontal, for example a floor, a walkway, driveway or a roof, or vertical, for example the walls of a building. For the purpose of the present application, the term "vertical" includes all non-zero slopes.

The material forming the structural layer may be internal or external. The structural layer may be porous or dense. Specific examples of structural layers include, for example, concrete, clay, ceramic (e.g. tiles), natural stone and other non-metals. Additional examples of the structural layer include roofs, for example metal roofs, roofing granules, synthetic roofing materials (e.g. composite and polymeric tiles) and asphalt shingles. The structural layer may also be a wall. In a specific embodiment, the coating is coated on a roofing granule and the inorganic copper compound is cuprous oxide. In those embodiments, the percent cuprous oxide is between 0.5 and 10 weight percent, between 0.5 and 6 weight percent or between 4 and 6 weight percent based on the weight of the coated granules.

Generally, the coating is coated on to the structural layer and then fired to insolubilize the binder. The firing temperature is generally less than 538° C. (1000° F.). Generally, the firing is done at temperatures in excess of 170° C.

The coatings of the invention provide long-term resistance to staining from bio-organisms or from airborne contaminants.

EXAMPLES

These examples are merely for illustrative purposes only and are not meant to be limiting on the scope of the appended claims. All parts, percentages, ratios, etc. in the examples and the rest of the specification are by weight, unless noted otherwise.

Copper Extraction Test

The Copper Extraction test is used to compare the relative algaecidal performance of different samples containing copper particles. A sample that retains less copper after performing the extraction test a number of successive times, indicates an improved release of copper that is available for algae control. The amount of copper extracted corresponds to the amount of copper available as an algaecidal ingredient on a roof protected with algae resistant shingles. To be effective, the copper generally needs to be extracted at a rate sufficient to prevent the growth of algae on the sample, however, the rate must also be sufficiently low to enable the amount of copper included in the sample to continue being effective for as many as 5 to 10 and even 20 years of exposure to typical dew and rainfall.

The copper containing granules to be tested were screened to provide a size cut that passed through 16 mesh and were retained on 20 mesh US Standard screen sieves. The initial copper content of the screened granules was determined by placing 15 grams (g) of the screened granules into a polyethylene snap-ring, holding ring, 31 mm diameter, open-ended cup (Spex CertiPrep, Metuchen, N.J.). The base of the assembled sample cup was lined with polypropylene window film, 0.2 mil (5 micrometers) thick, 2⅞ inches wide (7.3 cm) (Spex CertiPrep, Metuchen, N.J.). Taking care not to tap or otherwise cause the granules to rearrange in the cup, the cup was placed onto the probe of a Spectro Titan X-ray Fluorescence (XRF) instrument (available from Spectro Analytical Instruments inc., Marble Falls, Tex.). Sample time was set to 20 seconds, averaging 4 separate measurements. The instrument had been calibrated with a series of granules of known copper content and data is reported in units of g copper extracted/2 kg granules.

Fifty grams of screened granules were placed into a 500 mL Erlenmeyer flask containing 200 mL of a boiling 5% $Al_2(SO_4)_3$ solution. The granules were allowed to boil in the aluminum sulfate solution for exactly 10 minutes. The flask was then removed from the hot plate and the supernatant immediately decanted. Care was taken not to lose any of the granules from the flask. The granules were rinsed three times with 200 mL deionized water, taking care with each decantation to avoid granule loss. The granules were placed on a paper towel on a drying rack in an oven for 12 minutes at 230° F. (110° C.). Granules were then removed from the oven, allowed to cool and the final copper content again determined according to the method described above. The difference between the XRF readings before and after extraction is reported as the extracted amount. The units are g copper extracted/2 kg granules.

Granule Coating Method

The slurry components indicated in Table 2 were combined in a vertical mixer. 1000 parts by weight of substrate were pre-heated to 90-95° C. and then combined with the indicated amount of slurry in a vertical or horizontal mixer. The slurry coated granules were then fired in a rotary kiln (natural gas/oxygen flame) with a set point 850° F. (454° C.) over a period of about 10 to 20 minutes. For multiple coats, the procedure above is repeated using the coated granules as the substrate. Following the firing of the final coat, the granules were allowed to cool to 100° C., and post-treated to reduce dust generation during processing and to improve adhesion to substrates, such as asphaltic shingles. Typical treatments, though not the subject of the present invention, include oils, such as silicone oil, and naphthenic oil such as available from Cross Oil & Refining and Marketing Inc, Smackover, Ark. The granules are then placed in an oven at 176° F. (80° C.) for 1 hour.

Materials

The following materials were used in the Examples:

Sodium silicate solution (39.4% solids, 2.75 ratio $SiO_2$ to $Na_2O$) available from PQ Corp., Valley Forge, Pa.

Borax (Sodium Borate, 5 Mol, typical composition: 21.7% $Na_2O$, 48.8% $B_2O_3$, and 29.5% $H_2O$) available from U.S. Borax, Boron, Calif.

Carbon black Raven 410 beads, pigment available from Columbian Chemicals co, Marietta, Ga.

Burnt Umber L1361, pigment available from Rockwood Pigments, Beltsville, Md.

Zinc oxide 911 kadox, pigment available from Horsehead Corp, Monaca, Pa.

Chromium oxide 112, pigment available from Elementis Chromium lp, Corpus Christie, Tex.

Titanium dioxide SMC1125, pigment available from Special Materials Company, Cherry Hill, N.J.

Grade #11 uncoated roofing granules (available from 3M Company, St. Paul, Minn.)

Cuprous Oxide ($Cu_2O$) available from: American Chemet, East Helena, Mont., First Continental International, Rochelle Park, N.J., and Nordox AS, Oslo, Norway Sodium Lauryl Sulfate ("Sulfochem SLS") available from Chemron Corporation, Paso Robles, Calif.

Kaolin clay available as Wilklay RP2 from Wilkinson Kaolin Associates ltd, Gordon, Ga.

Particle size distributions were measured on five different samples of Cuprous Oxide from the three suppliers. A Beckman Coulter Multisizer™ 3 instrument equipped with a 70 micrometer aperture tube was used to characterize particle size distribution. Samples were suspended in Isoton 2 water with 3 drops of Coulter Dispersant Type 1A Nonionic (both available from Beckman Coulter). Approximately 1 ml of the suspended samples were pipetted into the beaker of Isoton 2 water in the analyzer with the stirrer set at a medium speed. Samples were counted until a minimum of 100,000 counts were reached, using 300 size bins ranging from 1.43 to 42 microns. The data for these measurements is included in Table 1 below. Sample 5 had a median particle size below the minimum bin size for the Coulter method as described above. All cuprous oxide samples were also analyzed using the BET (Brunauer, Emmit, and Teller) technique for measuring surface area using a Quantchrome Autosorb-1 instrument to measure nitrogen gas physical adsorption onto the samples. The results from this analysis are included in Table 1 below.

TABLE 1

Cuprous Oxide Particle Size (micrometer) Distribution Statistics and Surface Area (meters squared per gram)

| | Sample | | | | |
|---|---|---|---|---|---|
| | 1 | 2 | 3 | 4 | 5 |
| Supplier | First Continental International | American Chemet | American Chemet | Nordox | Nordox |
| Mean: | 4.63 | 8.21 | 5.48 | 3.60 | Not Measured |
| Median: | 3.05 | 7.20 | 5.15 | 3.34 | Not Measured |
| Mode: | 2.96 | 12.23 | 6.22 | 3.58 | Not Measured |
| S.D.: | 4.62 | 5.16 | 2.66 | 1.96 | Not Measured |
| Variance: | 21.34 | 26.64 | 7.10 | 3.85 | Not Measured |
| C.V.: | 99.70 | 62.90 | 48.65 | 54.41 | Not Measured |
| Skewness: | 2.64 | 1.90 | 1.65 | 3.50 | Not Measured |
| Surface area: | 1.175 | 0.1267 | 0.2247 | 0.6729 | 2.354 |

TABLE 2

Composition of coating slurries (parts by weight)

| | Formulation 1 | | Formulation 2 | |
|---|---|---|---|---|
| | | | First and Second | |
| | First coat | Second Coat | coat | Third Coat |
| Grade #11 roofing granules | 2000 (uncoated) | 2000 (w/ first coat) | 2000 | 2000 (w/ second coat) |
| Cuprous Oxide | 87.5 | | 66.5 | |
| Borax | 1.63 | 0.3 | 1.24 | 0.3 |
| Kaolin clay | 35 | 13.33 | 26.6 | 13.33 |
| Chromium oxide | 3.13 | 2.33 | 0 (1st) 2.38 (2nd) | 2.33 |
| Sodium silicate solution | 70 | 24 | 53.2 | 24 |
| Water | 35 | 17.5 | 26.6 | 17.5 |
| Sodium Lauryl Sulfate | 0.04 | | 0.03 | |
| Carbon Black | | 0.1 | | 0.1 |
| Burnt Umber | | 1.33 | | 1.33 |
| Zinc oxide | | 1 | | 1 |
| Titanium dioxide | | 2.33 | | 2.33 |

Example 1

Grade #11 roofing granules were prepared with the coating as indicated above under Formulation 1, using the Cuprous Oxide Sample 1 (median size of 3.05 microns). The Copper Extraction test described above was performed 10 successive times, and the total amount of copper extracted was calculated and is shown in Table 3.

Comparative Example A

Grade #11 roofing granules were prepared with the coating as indicated above under Formulation 1, using the Cuprous Oxide Sample 2 (median size of 7.2 microns). The Copper Extraction test described above was performed 10 successive times, and the total amount of copper extracted was calculated and is shown in Table 3.

Comparative Example B

Grade #11 roofing granules were prepared with the coating as indicated above under Formulation 2, using the Cuprous Oxide Sample 2 (median size of 7.2 microns). This formulation retains the same ratios of cuprous oxide to clay and silicate solutions but results in a final product which has 1.5 times the amount of cuprous oxide compared to Formulation 1. The Copper Extraction test described above was performed 10 successive times, and the total amount of copper extracted was calculated and is shown in Table 3.

TABLE 3

| | Example 1 | Comparative Example A | Comparative Example B |
|---|---|---|---|
| Copper Extraction Test | 25 grams per kilogram of coated granules | 14 grams per kilogram of coated granules | 21 grams per kilogram of coated granules |

Example 2

A Box-Behnken designed experiment was conducted varying the clay-silicate ratio, copper concentration, and cuprous oxide particle size. In this example, there were three slurry coating steps. For each of the design points, the substrate parts by weight was 2000 (uncoated Grade #11 roofing granules were coated with the first slurry); the second slurry coat composition was based on the substrate weight including the first coating, and the third slurry coat composition was based on the substrate weight including the first two coatings. The first coating slurry in each design point contained all of the components in the quantities identified in Table 4 with the exception of Chromium Oxide (zero Chromium Oxide), the second coating slurry in each design point contained all of the components in the quantities identified with the amount of Chromium Oxide indicated in Table 4, and the third coating slurry in each design point was identical.

The third slurry coat was identical for each of the design point and contained all of the components in the quantities identified in Table 4A.

TABLE 4A

| Borax | 0.3 |
|---|---|
| Kaolin Clay | 13.33 |
| Sodium Silicate solution | 24.00 |
| Water | 17.5 |
| Carbon Black | 0.1 |
| Burnt Umber | 1.33 |
| Zinc Oxide | 1 |
| Chromium Oxide | 2.33 |
| Titanium Dioxide | 2.33 |

The Copper Extraction test described above was performed 10 successive times on each of the design points, and averaged for each of the Cuprous Oxide mean particle sizes. The analysis of the Box-Behnken design showed that the particle size of cuprous oxide was a significant factor in the copper extraction rate. The rate initially showed no significant change below a median particle size of less than 7 and then surprisingly increased as the particle size decreased below a median particle size of 5 micrometers.

TABLE 4

Box-Behnken designed experiment slurry compositions - parts by weight per 2000 parts substrate

| | A | B | C | D | E | F | G | H | I | J | K | L | M | N | O |
|---|---|---|---|---|---|---|---|---|---|---|---|---|---|---|---|
| Cuprous Oxide Sample 1 | | | | 71.36 | | | 81.36 | 84.00 | | | | | | 70.00 | |
| Cuprous Oxide Sample 3 | 65.42 | 76.36 | | | | 78.50 | | | 76.36 | | 89.50 | 76.36 | 74.58 | | |
| Cuprous Oxide Sample 2 | | | 84.00 | | 81.36 | | | | | 70.00 | | | | | 71.36 |
| Borax | 1.30 | 1.30 | 1.30 | 1.30 | 1.30 | 1.30 | 1.30 | 1.30 | 1.30 | 1.30 | 1.30 | 1.30 | 1.30 | 1.30 | 1.30 |
| Kaolin Clay | 22.50 | 28.00 | 28.00 | 22.50 | 33.50 | 22.50 | 33.50 | 28.00 | 28.00 | 28.00 | 33.50 | 28.00 | 33.50 | 28.00 | 22.50 |
| Chromium Oxide* | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 |
| Sodium Silicate solution | 56.00 | 56.00 | 56.00 | 56.00 | 56.00 | 56.00 | 56.00 | 56.00 | 56.00 | 56.00 | 56.00 | 56.00 | 56.00 | 56.00 | 56.00 |
| Water | 28 | 28 | 28 | 28 | 28 | 28 | 28 | 28 | 28 | 28 | 28 | 28 | 28 | 28 | 28 |
| Sodium Lauryl Sulfate | 0.03 | 0.03 | 0.03 | 0.03 | 0.03 | 0.03 | 0.03 | 0.03 | 0.03 | 0.03 | 0.03 | 0.03 | 0.03 | 0.03 | 0.03 |

Example 3

Grade #11 roofing granules were prepared with the 2 coatings indicated in Table 5 using the Cuprous Oxide Sample 4 (surface area of 0.6729 meters squared per gram). The Extraction test was performed 10 successive times, and the total amount of copper extracted was calculated to be 27 grams per kilogram of coated granules.

Example 4

Grade #11 roofing granules were prepared with the 2 coatings indicated in Table 5 using the Cuprous Oxide sample 5 (surface area of 2.354 meters squared per gram). The Extraction test was performed 10 successive times, and the total amount of copper extracted was calculated to be 37 grams per kilogram of coated granules.

TABLE 5

Composition of coating slurries (parts by weight) for Examples 3 and 4

| | First coat | Second Coat |
|---|---|---|
| Grade #11 roofing granules | 2000 (uncoated) | 2000 (w/ first coat) |
| Cuprous Oxide | 87 | |
| Borax | 1.6 | 0.3 |
| Kaolin clay | 35 | 13.33 |
| Chromium oxide | 0 | 1.6 |
| Sodium silicate solution | 70 | 24 |
| Water | 35 | 17.5 |
| Sodium Lauryl Sulfate | 0.04 | |
| Burnt Umber | | 0.1 |
| Zinc oxide | | 1 |
| Titanium dioxide | | 0.6 |

Although the present invention has been described with reference to preferred embodiments, workers skilled in the art will recognize that changes may be made in form and detail without departing from the spirit and scope of the invention.

What is claimed is:

1. A coating composition comprising an alkali metal silicate binder and inorganic copper compound particles wherein the particles have a median particle size of greater than 1 micrometer and less than 4 micrometers.

2. The coating composition of claim 1, wherein the particles have a median particle size of greater than 1 micrometer and less than 3 micrometers.

3. The coating composition of claim 1, wherein the particles have a median particle size of greater than 2.5 micrometers and less than 4 micrometers.

4. The coating composition of claim 1, wherein the particles have a median particle size of greater than 2.8 micrometer and less than 4 micrometers.

5. The coating composition of claim 1, wherein the copper compound is cuprous.

6. The coating composition of claim 5, wherein the copper compound is cuprous oxide.

7. The coating composition of claim 1, wherein the copper compound is cupric.

8. The coating composition of claim 7, wherein the copper compound is cupric oxide.

9. A coating composition comprising an alkali metal silicate binder and inorganic non-photocatalytic copper compound particles, wherein the particles have a median particle size of greater than 1 micrometer and less than 4 micrometers.

10. A structural layer comprising the coating of claim 1.

11. The structural layer of claim 10, wherein the structural layer is porous.

12. The structural layer of claim 10, wherein the structural layer is formed from concrete.

13. The structural layer of claim 10, wherein the structural layer is formed from clay.

14. The structural layer of claim 10, wherein the structural layer is formed from ceramic.

15. The structural layer of claim 10, wherein the structural layer is a tile.

16. The structural layer of claim 10, wherein the structural layer is horizontal.

17. The structural layer of claim 10, wherein the structural layer is vertical.

18. The structural layer of claim 10, wherein the structural layer is a roof.

19. The structural layer of claim 10, wherein the structural layer is a metal roof.

20. The structural layer of claim 10, wherein the structural layer is a roofing granule.

21. The structural layer of claim 10, wherein the structural layer is an asphalt shingle.

22. The structural layer of claim 10, wherein the structural layer is a metal tile.

23. The structural layer of claim 10, wherein the structural layer is a polymeric roofing tile.

24. The structural layer of claim 10, wherein the structural layer is a wall.

25. The structural layer of claim 10, wherein the structural layer is an interior construction surface.

26. The structural layer of claim 10, wherein the structural layer is an exterior construction surface.

27. A structural layer comprising the coating of claim 9.

28. The structural layer of claim 27, wherein the structural layer is porous.

29. The structural layer of claim 27, wherein the structural layer is formed from concrete.

30. The structural layer of claim 27, wherein the structural layer is formed from clay.

31. The structural layer of claim 27, wherein the structural layer is formed from ceramic.

32. The structural layer of claim 27, wherein the structural layer is a tile.

33. The structural layer of claim 27, wherein the structural layer is horizontal.

34. The structural layer of claim 27, wherein the structural layer is vertical.

35. The structural layer of claim 27, wherein the structural layer is a roof.

36. The structural layer of claim 35, wherein the structural layer is a metal roof.

37. The structural layer of claim 27, wherein the structural layer is a roofing granule.

38. The structural layer of claim 27, wherein the structural layer is an asphalt shingle.

39. The structural layer of claim 27, wherein the structural layer is a metal tile.

40. The structural layer of claim 27, wherein the structural layer is a polymeric roofing tile.

41. The structural layer of claim 27, wherein the structural layer is a wall.

42. The structural layer of claim 27, wherein the structural layer is an interior construction surface.

43. The structural layer of claim 27, wherein the structural layer is an exterior construction surface.

44. A coating composition comprising an alkali metal silicate binder and inorganic copper compound particles, wherein the particles have a median particle size of greater than 1 micrometer and less than 4 micrometers and the particles have surface area of greater than 0.3 $m^2$/gram.

45. The coating composition of claim 44, wherein the particles have a surface area greater than 0.5 $m^2$/gram.

46. The coating composition of claim 44, wherein the particles have a surface area greater than 1 $m^2$/gram.

47. The coating composition of claim 44, wherein the particles have a surface area greater than 2 $m^2$/gram.

* * * * *

UNITED STATES PATENT AND TRADEMARK OFFICE
CERTIFICATE OF CORRECTION

Page 1 of 1

PATENT NO.        : 8,808,756 B2
APPLICATION NO.   : 12/444800
DATED             : August 19, 2014
INVENTOR(S)       : Rachael Gould et al.

It is certified that error appears in the above-identified patent and that said Letters Patent is hereby corrected as shown below:

In the Claims

Column 9
Line 67, in Claim 1, delete "particles" and insert -- particles, --, therefor.

Column 10
Line 66, in Claim 19, delete "claim 10," and insert -- claim 18, --, therefor.

Signed and Sealed this
Third Day of February, 2015

Michelle K. Lee
*Deputy Director of the United States Patent and Trademark Office*